(12) United States Patent
Solomon et al.

(10) Patent No.: US 6,261,271 B1
(45) Date of Patent: *Jul. 17, 2001

(54) ANTI-INFECTIVE AND ANTITHROMBOGENIC MEDICAL ARTICLES AND METHOD FOR THEIR PREPARATION

(75) Inventors: Donald D. Solomon, Spring Valley; M. Parke Byron, Centerville, both of OH (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/006,677

(22) Filed: Jan. 13, 1998

Related U.S. Application Data (63) Continuation of application No. 08/487,795, filed on Jun. 7, 1995, now Pat. No. 5,707,366, which is a continuation of application No. 07/980,984, filed on Nov. 24, 1992, now Pat. No. 5,451,424, which is a continuation of application No. 07/586,171, filed on Sep. 21, 1990, now Pat. No. 5,165,952, which is a continuation of application No. 07/497,780, filed on Mar. 21, 1990, now Pat. No. 5,013,306, which is a continuation-in-part of application No. 07/298,392, filed on Jan. 18, 1989, now abandoned.

(51) Int. Cl.$^7$ ........................................................ A61M 5/32
(52) U.S. Cl. ........................................................... 604/265
(58) Field of Search .................................... 604/264, 265, 604/280, 266, 48, 93.01; 623/1.38, 1.42, 1.43, 1.44–1.46; 600/29–30; 524/916, 195; 523/112, 122; 427/2.1–2.3; 424/78.08

(56) References Cited

U.S. PATENT DOCUMENTS

| | | |
|---|---|---|
| 3,457,098 | 7/1969 | Leininger et al. . |
| 3,566,874 | 3/1971 | Shepherd et al. . |
| 3,604,426 | 9/1971 | Erickson . |

(List continued on next page.)

FOREIGN PATENT DOCUMENTS

| | | |
|---|---|---|
| 0229862 | 7/1987 | (EP) . |
| 0328421 | 8/1989 | (EP) . |
| 2084466 | 4/1982 | (GB) . |
| 59-227824 | 12/1984 | (JP) . |
| 59-228856 | 12/1984 | (JP) . |
| 60-36062 | 2/1985 | (JP) . |
| 60-36064 | 2/1985 | (JP) . |
| 20344/88 | 1/1988 | (JP) . |
| WO 86/02561 | 5/1986 | (WO) . |

OTHER PUBLICATIONS

The Condensed Chem. Dictionary, 546, 713, 840–841, 10th Edition, G.G. Kawlaley, Van Nostrand Reinhold Co., (1981).

Zdrahala et al., "Thermoplastic Polyurethanes. Materials for Vascular Catheters.", *Polyurethanes in Biomedical Engineering II*, H. Planck et al. (Eds.), Elsevier Science Publishers B.V., Amsterdam, The Netherlands (1987).

(List continued on next page.)

*Primary Examiner*—Sharon Kennedy
*Assistant Examiner*—Catherine Serke
(74) *Attorney, Agent, or Firm*—Hoffmann & Baron, LLP (57) ABSTRACT

An anti-infective medical article has chlorhexidine bulk distributed throughout a polyurethane base layer and may have a coating layer on the base layer. The coating layer may be chlorhexidine permeated into the surface or it may be an antibiotic, antithrombogenic agent or a polymeric surface layer laminated onto the base layer. The invention includes a method for preparing the article wherein a homogeneous melt of polymer and chlorhexidine is prepared by twin screw compounding and the melt is extruded to give a medical article having bulk distributed chlorhexidine.

43 Claims, 3 Drawing Sheets

U.S. PATENT DOCUMENTS

| | | |
|---|---|---|
| 3,695,921 | 10/1972 | Shepherd et al. . |
| 3,699,956 | 10/1972 | Kitrilakis et al. . |
| 3,705,938 | 12/1972 | Hyman et al. . |
| 3,822,238 | 7/1974 | Blair et al. . |
| 3,846,353 | 11/1974 | Grotta . |
| 3,987,797 | 10/1976 | Stephenson . |
| 4,054,139 | 10/1977 | Crossley . |
| 4,186,745 | 2/1980 | Lewis et al. . |
| 4,318,947 | 3/1982 | Joung . |
| 4,371,684 | 2/1983 | Quiring et al. . |
| 4,381,380 | 4/1983 | Leveen et al. . |
| 4,442,133 | 4/1984 | Greco et al. . |
| 4,446,124 | 5/1984 | Fox, Jr. et al. . |
| 4,460,369 | 7/1984 | Seymour . |
| 4,479,795 | 10/1984 | Mustacich et al. . |
| 4,515,593 | 5/1985 | Norton . |
| 4,521,564 | 6/1985 | Solomon et al. . |
| 4,535,078 | 8/1985 | Fox, Jr. et al. . |
| 4,539,234 | 9/1985 | Sakamoto et al. . |
| 4,544,547 | 10/1985 | von Bittera et al. . |
| 4,557,724 | 12/1985 | Gregonis et al. . |
| 4,563,485 | 1/1986 | Fox, Jr. et al. . |
| 4,581,028 | 4/1986 | Fox, Jr. et al. . |
| 4,581,390 | 4/1986 | Flynn . |
| 4,600,652 | 7/1986 | Solomon et al. . |
| 4,603,152 | 7/1986 | Laurin et al. . |
| 4,612,337 | 9/1986 | Fox, Jr. et al. . |
| 4,642,242 | 2/1987 | Solomon et al. . |
| 4,642,267 | 2/1987 | Creasy et al. . |
| 4,675,347 | 6/1987 | Mochizuki et al. . |
| 4,676,975 | 6/1987 | McGary et al. . |
| 4,677,143 | 6/1987 | Laurin et al. . |
| 4,678,660 | 7/1987 | McGary et al. . |
| 4,713,402 | 12/1987 | Solomon . |
| 4,723,950 | 2/1988 | Lee . |
| 4,729,914 | 3/1988 | Kliment et al. . |
| 4,749,585 | 6/1988 | Greco et al. . |
| 4,769,013 | 9/1988 | Lorenz et al. . |
| 4,806,621 | 2/1989 | Kohn et al. . |
| 4,853,978 | 8/1989 | Stockum . |
| 4,886,505 | 12/1989 | Haynes et al. . |
| 4,925,668 | 5/1990 | Khan et al. . |
| 4,999,210 | 3/1991 | Solomon et al. . |
| 5,013,306 | 5/1991 | Solomon et al. . |
| 5,019,096 * | 5/1991 | Fox et al. .................................. 623/1 |
| 5,089,205 | 2/1992 | Huang et al. . |

OTHER PUBLICATIONS

Solomon et al., "Antibiotic Releasing Polymers", *Journal of Controlled Release*, 6, 343–352 (1987.

Grasel et al., "Surface Properties and Blood Compatibility of Polyurethaneureas", Butterworth & Co. (Publishers) Ltd. (1986).

Coventry et al., "Experimental Use of a Slow Release Device Employing Chlorhexidine Gluconate in Areas of Acute Periodontal Inflammation", *Journal of Clinical Periodontology*, 9, 129–133 (1982).

Seko et al., "Efficacy of a Latex Foley Catheter with Sustained Release of Chlorhexidine: 1st Report: Clinical Trails for Prevention of Urinary Tract Infection".

Trookskin et al., "Prevention of Catheter Sepsis by Antibiotic Bonding", *Surgery*, 547–551 (1985).

Lazarus te al., "A Hydrophilic Polymer–Coated Antimicrobial Urethral Catheter", *J. Biomed. Mater. Res.*, 5, 129–138 (1971).

Maki et al., "Comparison of 70% Alcohol, 10% Povidone–Iodine and 25% Chlorhexidine for Cutaneous Disinfection in IV Therapy" (Abstract).

Tuominen et al., "The Effect of Local Antiseptic, Chlorhexidine in Preventing Infection from Central Venous Catherization", *Annals of Clinical Research*, 13, 425–428 (1981).

Judgement in Patent Interference No. 103,340, mailed: Jun. 22, 1994.

* cited by examiner

ANTI-INFECTIVE AND ANTITHROMBOGENIC MEDICAL ARTICLES AND METHOD FOR THEIR PREPARATION

This is a continuation of application Ser. No. 08/487,795 filed on Jun. 7, 1995, now U.S. Pat. No. 5,707,366, which is a continuation of Ser. No. 07/980,984 filed on Nov. 24, 1992, U.S. Pat. No. 5,451,424, which is a continuation of 07/586,171 filed on Sep. 21, 1990, U.S. Pat. No. 5,165,952, which is a continuation of Ser. No. 07/497,780 filed Mar. 21, 1990, U.S. Pat. No. 5,013,306, which is a continuation-in-part of Ser. No. 07/298,392 filed Jan. 18, 1989, now abandoned.

BACKGROUND OF THE INVENTION

1. Field of the Invention

This invention related to medical articles, and, more particularly, relates to articles which inhibit or reduce bacterial growth and the development of thrombi in a living body during their use and to their preparation.

2. Background of the Invention

Plastic medical articles intended for insertion into a patient must have a smooth surface to minimize patient discomfort. Another desirable feature of such articles is some means to control infection, which is a frequent complication during use of medical articles which come into contact with a body tissue or fluid. For example, infection remains a lethal complication of vascular prosthetic grafting. Catheters used for vascular access, both arterial and venous, abdominal cavity tubing, drainage bags, and various connectors are common sources of infection. In particular, a high percentage of patients who require long-term urinary catheters develop chronic urinary tract infections, frequently in conjunction with episodes of fever, chills, and flank pain. Such patients are at risk of developing bacteremia or chronic pyelonephritis, conditions of high morbidity and mortality.

Medical articles are frequently fabricated from polyurethane by molding and extruding techniques. A frequent problem, particularly during extrusion, is the difficulty of obtaining homogeneous melts free of gel particles which adversely affect the smoothness of the surface of the extruded product. A discussion of these problems is given in U.S. Pat. No. 4,371,684 to Quiring et al.

Many attempts to solve the problem of infection have been directed toward adherence of an antibacterial agent to the plastic article. Gould et al., in U.S. Pat. No. 3,695,921, discloses a catheter coated with a layer of hydrophilic polymer having an antibiotic absorbed therein.

EP published application 229,862 teaches thermoplastic polyurethane medical devices having an antimicrobial agent on its surface.

Fox et al. in U.S. Pat. No. 4,581,028, teaches infection resistance plastic medical articles, such as vascular grafts, having incorporated antimicrobial agents, such as silver sulfadiazine and pipericillin. The articles are prepared by dipping procedures.

Mustacich et al., in U.S. Pat. No. 4,479,795, discloses medical devices of permeable polymers including a releasably incorporated coating of a carboxylate antimicrobial agent which diffuses to the surface of the device to form an antimicrobial barrier.

In Japanese Patent Application No. SHO-60-36064 a polyurethane or silicone catheter is dipped into an aqueous solution of chlorhexidine to absorb the chlorhexidine into the polymer. The chlorhexidine is then converted to a water insoluble form by dipping into a solution of an acid. Japanese Patent No. 59,228,856 discloses an elastomer catheter having a water insoluble biguanide or salt thereof incorporated as a thin coating membrane in the surface of the catheter.

PCT published application No. WO 86,02561 teaches a medical device of a hydrophobic thermoplastic polymer having up to 1% chlorhexidine base coated thereon or incorporated therein.

UK Patent Application No. 2,084,466A discloses a polypropylene article rendered biocidal with chlorhexidine base, and suggests that the article may be prepared from other plastics.

Solomon et al., in U.S. Pat. No. 4,713,402, discloses a method for attachment of a quaternary salt to the surface of a polymeric article and affixation of an antibiotic or anti-thrombogenic agent to the salt.

In U.S. Pat. Nos. 4,521,564 and 4,642,242, Solomon et al., discloses a polyurethane article having an antithrombogenic agent covalently bonded to an amine group in the article surface.

McGary et al., in U.S. Pat. No. 4,678,660, discloses a polyurethane article having coated thereon a layer of polyurethane alloy containing a dispersed complex of a quaternary salt with either an antithrombogenic agent or an antibiotic.

Although all of the above disclosures have addressed the problems of infection and thrombogenesis during use of medical articles, satisfactory solutions have not yet been disclosed, particularly for medical articles, such as catheters, to be introduced and advanced through body passages. The present invention is directed toward providing a solution.

SUMMARY OF THE INVENTION

A method for preparing an anti-infective medical article includes preparing a homogeneous melt of a substantially hydrophilic polymer and an anti-infective agent and extruding the melt through a die to form a medical article having the anti-infective agent distributed substantially evenly throughout the bulk of the polymer (hereinafter referred to as bulk distributed). The term anti-infective agent is herein intended to mean any agent which inhibits bacterial growth, and thus includes antibiotics, antibacterial agents, antiviral agents and antimicrobial agents. The extruded article may be steeped in a solution of chlorhexidine to provide the article with additional chlorhexidine as a coating permeated into the surface of the article. The melt is preferably prepared by blending polymer pellets and chlorhexidine until an even coating of chlorhexidine on the polymer is obtained, followed by heating to give a homogeneous melt. Most preferably, polymer pellets and chlorhexidine powder are simultaneously blended and melted by twin screw compounding to form the homogeneous melt. The melt may then be extruded from the compounder and chipped.

In another embodiment of the method of the invention, two polymer melts are prepared, at least one of which contains bulk distributed chlorhexidine. The two melts may then be coextruded to give a laminated article having chlorhexidine bulk distributed in at least one of the base or laminating layers.

The invention includes a method to render the article having bulk distributed chlorhexidine anti-thrombogenic by coating the article with a quarternary ammonium salt and reacting the coating of salt with an antithrombogenic agent.

Preferred polymers are siloxane-urethane copolymers, or, most preferably, polyurethanes and polyurethaneureas. The chlorhexidine may be either in the form of the free base or, preferably in the form of a salt such as the hydrochloride, acetate and gluconate.

Another aspect of the invention is a medical article having chlorhexidine base or a salt thereof bulk distributed throughout the article. The preferred article additionally has a layer of chlorhexidine, preferably a chlorhexidine salt, permeated into the surface of the article. Another embodiment of the article of the invention is a laminated article having two polymeric layers, at least one of which has chlorhexidine bulk distributed. Alternatively, the article having bulk distributed chlorhexidine may have a coating of an anti-infective or antithrombogenic agent on the base layer or on the laminating layer. The preferred article of the invention is a tubing, most preferably a catheter.

Thus, the invention provides a method to prepare an anti-infective article from a high melting hydrophilic polymer having mechanical properties providing advantages not afforded by hydrophobic polymers. The preferred article has a surface layer of chlorhexidine which is rapidly released and bulk distributed chlorhexidine which is released slowly providing a long lasting anti-infective effect.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, a significant reduction of infection associated with the use of medical articles is achieved by combining an anti-infective agent with the article. If the anti-infective agent can form a salt, the article of the invention is contemplated to include the salt form of the agent as well as the parent (nonsalt) form. A variety of anti-infective agents as known in the art may be used, including antibiotics such as penicillin and antibacterial agents such as silver sulfadiazine. In some cases, it may be desirable to provide dual anti-infective action with two or more agents. The invention will be described in terms of the preferred chlorhexidine, a biguanide of known safety and high activity against a wide variety of organisms, including gram negative and gram positive bacteria and yeasts, with the understanding that the invention contemplates any anti-infective agent which may be bulk distributed in the polymer by the method of the invention.

The medical article of the invention may be any medical article compatible with chlorhexidine which, absent the chlorhexidine, may lead to infection when in contact with a body tissue or fluid. Exemplary of, but not limited to, such articles are vascular access (arterial and venous) catheters, introducers, vascular grafts, urinary catheters and associated articles, such as drainage bags and connectors, and all abdominal cavity drainage tubing, bags and connectors. Preferred articles are polymeric, most preferably a hydrophilic polymeric vascular access catheter.

Selection of a polymer to be used for catheter fabrication requires a balancing of several properties. First, the catheter must be stiff enough to be inserted into, for example, a blood stream, without kinking. However, once in contact with the blood, it should preferably soften and become sufficiently flexible to bend and be advanced through the tortuous path of the vessel.

Polymers which exhibit suitable mechanical and hydrophilic behavior for fabrication of the catheter of the invention are, for example, substantially hydrophilic, polyurethanes, polyurethaneureas, and siloxane-urethane block copolymers. Preferred polymers are polyurethanes or polyurethaneureas having a resin hardness of about 50 A to 75 D when measured under standard room conditions of 23° C. and 50% relative humidity, and a water absorption capacity of about 1.0 to 6.0%, preferably about 1.5 to 3.0% (all percentages given herein are by weight unless otherwise stated). Exemplary of suitable polymers and their hardness and water absorption percentages are polyurethane 80 A (1.85%), polyurethane 55 D (1.66%), polyurethaneurea 70 A (1.94%), silicone-urethane copolymer 70 A (1.87%) and silicone-urethane copolymer 65 D (1.88%). Polyolefins in contrast are hydrophobic, absorbing about 0.04 to 0.4% water, and are unsuitable for the present invention because, as shown in Example XV, they remain rigid, inflexible and unable to advance through winding blood vessels without kinking or rubbing against the vessel wall causing irritation, patient discomfort and possibly phlebitis.

Various embodiments of the article having bulk distributed chlorhexidine are contemplated to fall within the scope of the invention. For example, the polymeric article may have a layer of chlorhexidine coated onto its surface, or the chlorhexidine may be bulk distributed in the article. A polymeric base layer, with or without bulk distributed chlorhexidine, may have one or more laminated layers of the same or another polymer thereon. Different properties may desirably be conferred on the article by use of different polymers. The laminated layers may or may not have bulk distributed chlorhexidine. The layers may be of different thickness and may have different concentrations of bulk distributed chlorhexidine or may have two or more different anti-infective agents. The preferred article of the invention has a layer of chlorhexidine coated onto the surface of the article and bulk distributed chlorhexidine therein.

Articles of the invention having bulk distributed chlorhexidine may be prepared by extruding a melt of the polymer and chlorhexidine through a die. The chlorhexidine may be melted or may be a solid uniformly distributed in the polymer melt. The melt to be extruded may contain about 0.05% to 10%, preferably about 1 to 5% by weight of chlorhexidine, and may be prepared in any suitable way. For example, the polymer and chlorhexidine may be melted, and the melts combined and mixed thoroughly. While blending of separate melts may be performed, this method is less preferred because the high viscosities of the melts make uniform blending difficult resulting in an article having a rough surface.

The preferred method for preparing the melt for extrusion is to blend the polymer and chlorhexidine in particulate form prior to melting. In general, particulate blending may be carried out by any suitable mixing technique, such as stirring the polymer pellets and chlorhexidine powder together, or, preferably, by tumbling. This method is straightforward and is the method of choice for preparation of melts of polyurethanes and chlorhexidine base. It has been found, however, that particular chlorhexidine salts and polyurethane pellets do not form uniform blends by these conventional procedures when the concentration of the salt is greater than about 1% by weight. If the salt and pellets are not uniformly blended prior to melting, the melt and therefore the extruded article will contain nonhomogeneously distributed salt and, as a consequence, significant areas of rough surface having little or no salt.

In order to prepare uniform blends of higher salt concentration, the polymer pellets may first be surface wetted by thorough mixing of the pellets with about 0.1 to 2% by weight of a polyol. Any suitable polyether or polyester polyol may be used, as, for example, polytetramethylene oxide (PTMO) having a molecular weight of about 500 to 3,000. These products are well-known and are commercially available.

A preferred method for blending chlorhexidine salts uniformly with polymer pellets is to melt and repelletize the ingredients with a twin screw compounder. The polymer pellets, chlorhexidine salt and other ingredients such as fillers and pigments, may be fed to the compounder at a suitable rate. In the compounder, the ingredients are melted and blended and then extruded into strands. The strands may be pelletized and dried prior to further processing. A corotating intermeshing twin screw extruder may be used, such as Model ZDSK-28 from Werner and Pfleiderer Corp., Ramsey, N.J.

The homogeneous pellets of polymer and chlorhexidine prepared as described above may be remelted and molded or extruded into the desired shape of the medical article. For the preferred catheter of the invention, the melt may be extruded into tubing using conventional equipment, such as, for example, a Killion extruder with a one inch diameter barrel and a 24:1 (1/d) screw.

The temperature processing range for uniform blends of particular chlorhexidine and polymer depend on the polymer being extruded. In general, melting and extrusion may be performed over a temperature range of about 160° to 250° C., preferably about 200°–235° C.

The article of the invention having bulk distributed chlorhexidine may be steeped in a solvent solution of chlorhexidine to permeate a layer of chlorhexidine into the surface of the article. An effective coating of chlorhexidine may be obtained when the steeping solution contains from about 1–25%, preferably 5–15% of chlorhexidine. Accordingly, the choice of solvent depends on the form of chlorhexidine being coated and on the temperature contemplated for the steeping solution. Suitable solvents to serve as the steeping medium for chlorhexidine base are water, methylene chloride and preferably methanol. For chlorhexidine salts, such as the hydrochloride, acetate, or preferably the gluconate, suitable solvents are methanol, ethanol and preferably water.

Steeping may be carried out for about 2 minutes to 2 hours at a temperature of about 15° to 60° C. In general, it has been found that steeping for about 15–30 minutes at about 50° C. gives a surface-permeated coating of chlorhexidine sufficient to provide anti-infective protection for vascular or other catheterization of about 1–14 days. It is, of course, evident that a chlorhexidine coating may be formed on either or both the outside and lumen walls of the catheter merely by contacting the desired walls with the steeping solution. Thus, steeping solution may be drawn into the lumen for contact with the lumen wall only, or the lumen may be filled with a solid rod so that the steeping solution contacts only the outside wall.

Another embodiment of the invention is a laminated catheter which includes a base polymer having coated thereon a polymeric layer containing bulk distributed chlorhexidine. If desired, chlorhexidine may also be bulk distributed in the base polymer. The laminated catheter of this embodiment of the invention may be prepared by coextrusion of polymer melts containing bulk distributed chlorhexidine prepared as described above. For example, the coextrusion unit disclosed in U.S. Pat. No. 4,581,390 to Flynn, may be used. Alternatively, a catheter having laminated polymeric layers on both sides of the base layer may be prepared by simultaneous extrusion of three layers through a suitable tri-layer die. Such a tri-layer tubing may have bulk distributed chlorhexidine in any one, two or all three of the layers, which may be of different thickness, or, if desired, a different agent may be either bulk distributed or surface coated onto one or both of the laminated layers.

The preferred catheter of the invention includes a polymer having both bulk distributed chlorhexidine and a chlorhexidine coating. This embodiment of the invention produces a dual anti-infective activity. The surface coating provides a readily available and rapid release of chlorhexidine. The bulk distributed chlorhexidine, due to the hydrophilic nature of the polymer, migrates slowly to the surface when the catheter is in contact with a body fluid and produces anti-infective activity of long duration.

For some applications of the anti-infective article of the invention, it may be desirable to include an antithrombogenic agent. Thus, another preferred article has chlorhexidine bulk distributed in the polymer and an antithrombogenic agent, such as dextran sulfate or, preferably heparin, coated thereon. A suitable method for ionically affixing heparin is that of Grode et al. (*Journal of Biomedical Materials Research Symposium*, 3, 77 (1972)) wherein a quaternary ammonium surface active agent such as, for example, tridodecylmethylammonium chloride, is permeated into the surface of the polymer and then reacted with sodium heparin. Another suitable method is that of Solomon et al. (U.S. Pat. No. 4,521,564) in which heparin is covalently attached to a polymeric surface containing an amino group.

Although the invention has heretofore been described in terms of the preferred chlorhexidine, the use of other anti-infective agents may confer desirable properties on the catheter of the invention. For example, an article having bulk distributed chlorhexidine may be surface coated with an antibiotic. Preparation of such an article may be carried out be permeating the polymer with a quarternary ammonium salt, as described above, and reacting the salt thereby affixed to the polymer surface with the desired antibiotic. Exemplary of antibiotics which are suitable for affixation to the article of the invention are penicillin, oxacillin, clindamycin, carbenicillin, cephalosporins, cefoxitin, cefazolin, dicloxacillin, cloxacillin and clavulanic acid and mixtures thereof.

Figure 1:
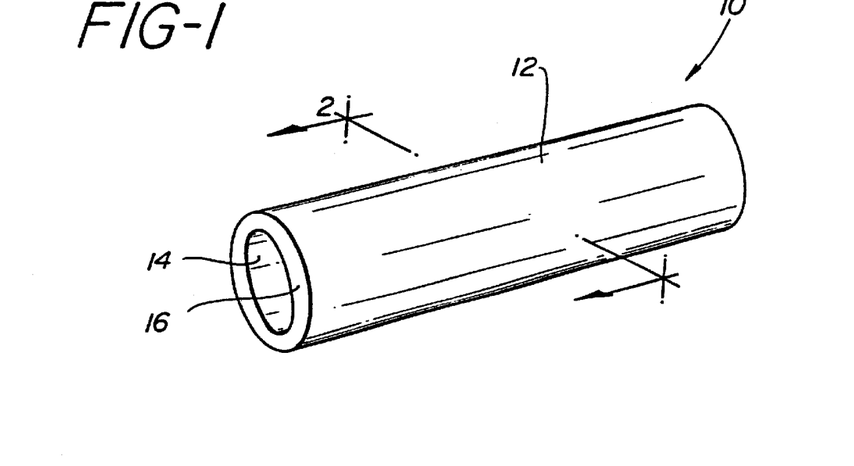
FIG. 1 is a perspective view of a typical polymeric tubing of the invention.
Figure 2:
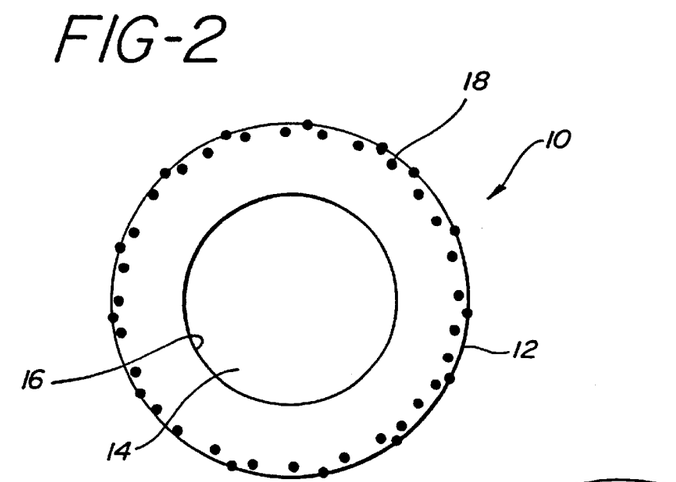
FIGS. 2–5 are cross-sectional views of the tubing of FIG. 1 taken along the line 2—2 thereof showing various embodiments of the tubing after application of chlorhexidine thereto.
Figure 3:
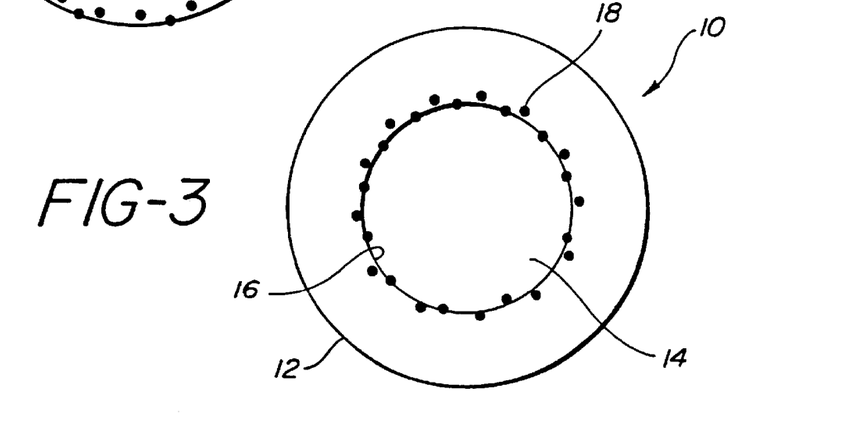

The anti-infective catheter prepared by the method of the invention will now be described in more detail with the aid of the drawings. In the following discussion of the drawings, elements identical or substantially similar to previously described elements are given the same reference number with a letter suffix. FIG. 1 shows polymeric catheter tubing 10 having an outside wall 12, a lumen 14 and a lumen wall 16. FIG. 2 shows tubing 10 having chlorhexidine molecules 18 permeated by steeping into the surface of outside wall 12, and FIG. 3 shows chlorhexidine molecules 18 permeated into the surface of lumen wall 16.

Figures 4, 5, 6:
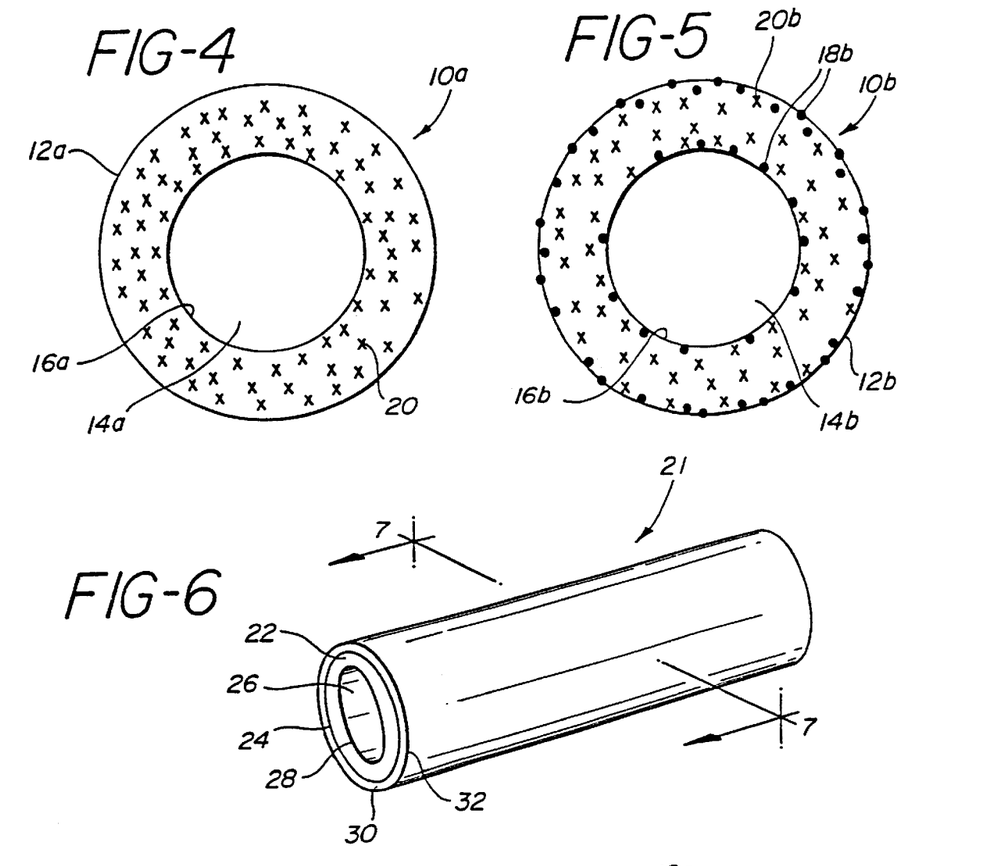
FIG. 6 is a perspective view of a laminated tubing of the invention.

FIG. 4 shows polymeric tubing 10a having an outside wall portion 12a, a lumen 14a and a lumen wall 16a. Chlorhexidine molecules 20 are bulk distributed throughout the polymer.

FIG. 5 illustrates a preferred catheter 10b of the invention. Catheter 10b has an outside wall 12b, a lumen 14b and a lumen wall 16b. Permeated into the surfaces of walls 12b and 16b are chlorhexidine molecules 18b. Chlorhexidine molecules 20b are bulk distributed in the catheter.

Figure 7:
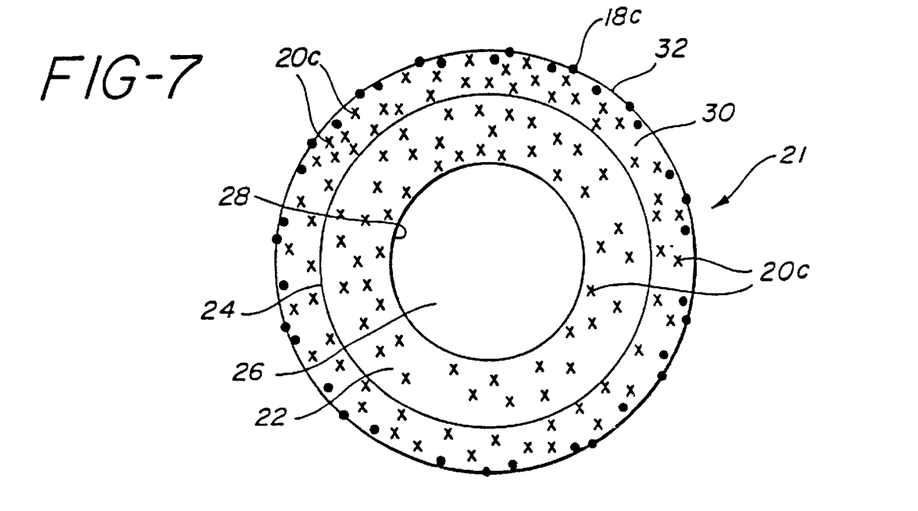
FIGS. 7–9 are cross-sectional views of the tubing of FIG. 6 taken along the line 7—7 thereof showing applied anti-infective agent.

Laminated anti-infective catheters in accordance with the invention are illustrated in FIGS. 6–9. In FIGS. 6 and 7, catheter 21 includes a base polymeric tubing 22 having an outside wall portion 24, a lumen 26 and a lumen wall 28. A polymeric laminating layer 30 having a surface 32 is coated onto base tubing 22. Chlorhexidine molecules 20c are bulk distributed in layers 22 and 30 and chlorhexidine molecules 18c are permeated into the surface of layer 30.

Figure 8:
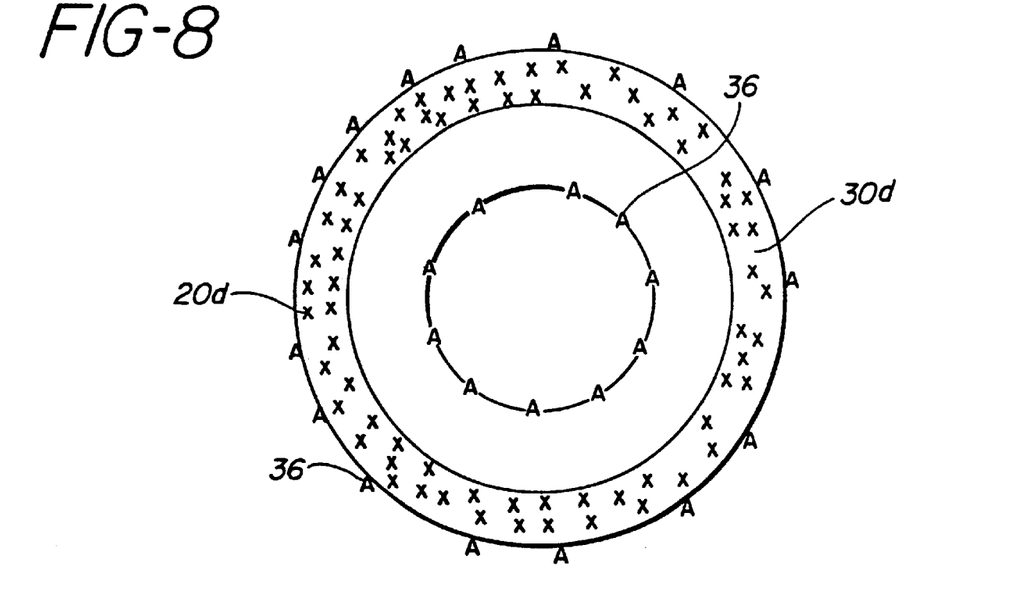

FIG. 8 illustrates a laminated catheter tubing having chlorhexidine molecules 20d bulk distributed in outer polymeric layer 30d and antibiotic molecules 36, indicated by the letter A permeated into the outside and lumen surfaces.

Figure 9:
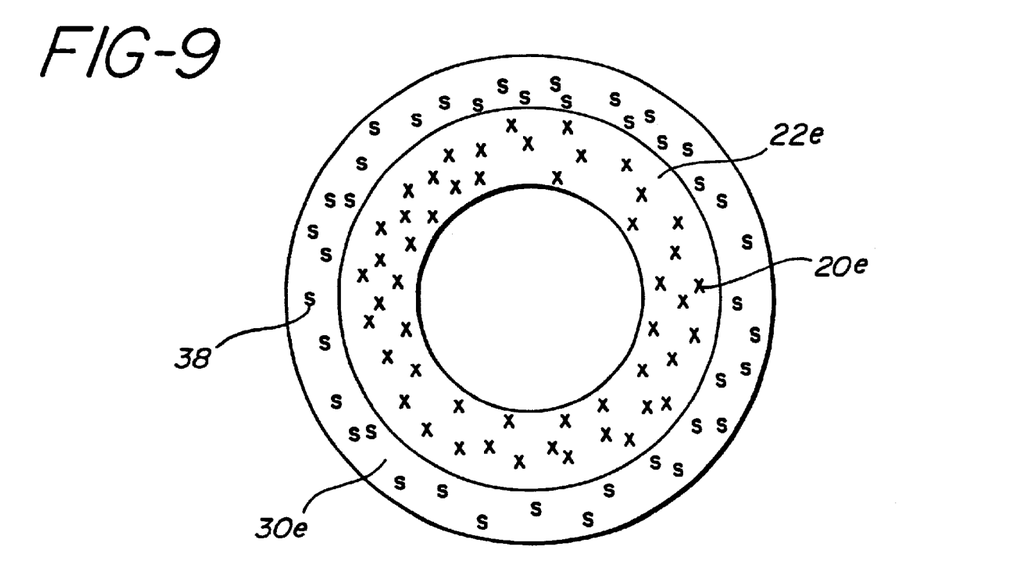

A laminated catheter tubing illustrated in FIG. 9 has bulk distributed chlorhexidine molecules 20e in the inner base layer 22e and bulk distributed molecules of silver sulfadiazine 38, indicated by the letter S in the laminating layer 30e.

The following examples are provided to further illustrate typical catheter preparations of the invention and both in vitro and in vivo procedures for determining their anti-infective properties.

EXAMPLE I

Preparation of Polyurethane Tubing Having Bulk Distributed Chlorhexidine Diacetate Polyurethane pellets were blended with 5% chlorhexidine diacetate powder with the Werner and Pfleiderer, Model ZDSK-28 twin screw compounder and the well blended mixture was extruded into 16 guage tubing using a Killion one inch extruder at approximately 175° C.

EXAMPLE II

Test for Anti-Infective Activity (In Vitro)

In vitro antimicrobial activity of the anti-infective tubing of the invention was measured by a standard zone of inhibition test. A broth of the test organism, such as *S. aureus*, was started from standard disks (Bactrol) in trypticase soy broth (TSB) and allowed to grow overnight. A 0.2 ml aliquot of the overnight broth was transferred to a fresh solution of TSB and allowed to grow for 2 to 5 hours until the turbidity of the solution was equivalent to a 1% barium sulfate standard solution. A 0.2 ml aliquot of this broth was transferred to a Mueller-Hinton (M-H) agar plate and spread evenly on the surface. Medical tubings of the invention were cut into suitable lengths of 1.5 cm and embedded into the surface of the agar. The plates were then cultured 16 hours (overnight). Plates were evaluated for the inhibition of bacterial growth visually by the unaided eye. Zones were measured in millimeters across the axis of the tubing, the measurement including the diameter of the medical article.

Tubing prepared as described in Example I above demonstrated the following antimicrobial activity in vitro.

| Organism | Zone, mm |
| --- | --- |
| *S. aureus* | 8.3 ± 1.3 |
| *S. epidermidis* | 12.3 ± 0.5 |
| *C. albicans* | 12.8 ± 0.5 |

Permanency of the chlorhexidine was evaluated using a saline leach study. The tubings of Example I were exposed to 37° C. normal saline for various lengths of time. At the appropriate time interval, samples were retrieved from the saline and placed on a prepared agar plate as described above. Zone sizes were measured as above to determine retained antimicrobial activity. The following results were obtained:

| Leach Time, hrs. | Zone of Inhibition, *S. aureus*, mm. |
| --- | --- |
| 0 | 11.3 ± 1.3 |
| 1 | 10.7 ± 1.2 |
| 4 | 9.3 ± 1.2 |
| 8 | 8.7 ± 0.6 |
| 24 | 7.7 ± 1.5 |

EXAMPLE III

Preparation of Polyurethane Tubing Having Bulk Distributed Chlorhexidine Dihydrochloride Polyurethane pellets were blended with either 4.0, 6.0 or 8.0 percent chlorhexidine dihydrochloride via the twin screw compounder. The blended material was then extruded into tubing and evaluated for in vitro antimicrobial activity against *S. aureus* using the zone of inhibition method described in Example II. The following results were obtained:

| Tubing, % Chlorhexidine | Zone, min. |
| --- | --- |
| 4.0 | 4.7 ± 0.6 |
| 6.0 | 6.0 ± 0.0 |
| 8.0 | 3.0 ± 1.0 |

EXAMPLE IV

Preparation of Polyurethane Tubing Having Both Bulk Distributed and surface Permeated Chlorhexidine Polyurethane polymer pellets and 3% chlorhexidine dihydrochloride were first blended via a twin screw compounder at approximately 200° C. The blended material was then extruded using standard tubing extrusion equipment at a temperature of approximately 175° C. A surface coating of chlorhexidine was provided by steeping the polyurethane tubing in a 10% aqueous solution of chlorhexidine digluconate for 15 minutes at 50° C. The finished tubing produced the following zone of inhibition results when evaluated according to Example II.

| Organism | Zone, mm |
|---|---|
| S. aureus | 15.0 ± 1.0 |
| C. albicans | 5.8 ± 3.6 |

EXAMPLE V

In Vivo Test for Anti-Infective Activity

The antimicrobial-containing tubings of Example I were evaluated for efficacy in vivo with a subcutaneous rabbit model. Sterile tubing samples were placed in a surgically created pocket on the shaved back of a rabbit which had been washed and cleaned with an antiseptic. The tubing was sutured in place to prevent the rabbit from removing it. A $1\times10^3$ inoculum of Staphylococcus aureus colony forming units (CFU) was injected into the subcutaneous pocket at the time of tubing insertion to initiate the test. Tubing samples were then retrieved from the rabbit over a period of days. Recovered samples were then quantitatively analyzed for the amount of S. aureus present using the method of Solomon and Sherertz, J. Controlled Release, 6 (1987) 343–352. Non-treated tubing samples were run concurrently as controls. The following results were obtained:

| | log CFU, indwelling time | | |
|---|---|---|---|
| Tubing | 4 days | 7 days | 14 days |
| Control | 2.37 ± 2.99 | 3.17 ± 3.48 | 3.44 ± 3.83 |
| Example I | 0.01 ± 0.00 | 0.72 ± 1.49 | 1.10 ± 1.48 |

EXAMPLE VI

Preparation of Laminated Polyurethane Tubing Having Bulk Distributed Chlorhexidine in Both Layers Polyurethane and polyurethaneurea polymer resins were separately processed through the twin screw compounder with 4% and 6% chlorhexidine hydrochloride respectively as described in Example IV, resulting in bulk distributed chlorhexidine in both polymers. The antimicrobial containing resins were then coextruded into tubing using standard equipment. The resulting tubing exhibited the following rates of release (determined as in Example II) of chlorhexidine from the internal and external tubing surfaces which are proportional to the resin's chlorhexidine content.

| | Release Rate, mm. of zone | |
|---|---|---|
| Hours | 4% | 6% |
| 0 | 4.0 | 6.5 |
| 1 | 2.7 | 5.8 |
| 2 | 2.3 | 3.8 |

EXAMPLE VII

Preparation of Laminated Polyurethane Tubing Having Bulk Distributed Chlorhexidine in the Outer Layer Only Polyurethane polymer pellets and 5% chlorhexidine dihydrochloride were first blended via the twin screw compounder as described in Example IV. The antimicrobial-containing resin was then coextruded along with a non-antimicrobial containing resin such that the lumen surface of the tubing did not contain any antimicrobial. The outer tubing layer thus provided antimicrobial activity to prevent or reduce microbial migration through the catheter wound tunnel, while the inner lumen was chlorhexidine free, thereby eliminating potentially adverse reactions such as intravenous infusion (drug)-chlorhexidine interactions.

EXAMPLE VIII

Preparation of Polyurethane Tubing Having Both Bulk Distributed Chlorhexidine and Heparinized Surfaces Polyurethane polymer pellets and 6% chlorhexidine dihydrochloride were first blended via a twin screw compounder as described in Example IV. Bulk distributed antimicrobial tubing was then extruded into 16 guage tubing using standard equipment. The tubing was then treated according to the method of Grode et al. (supra) using tridodecyl (methylammonium chloride) to provide an ionically bonded heparin coating to both the inner and outer tubing surfaces, thus yielding a catheter tube with both antimicrobial and antithrombogenic properties. The tubing produced the following in vitro antimicrobial effects.

| Organism | Zone of Inhibition, mm |
|---|---|
| S. aureus | 3.5 ± 0.6 |
| C. albicans | 6.3 ± 1.2 |

The tubing also demonstrated antithrombogenic efficacy as shown by a partial thromboplastin time of greater than 1800 seconds extension when determined by the procedure of B. A. Brown, Hematology Principles and Procedures, Third Edition, Lea and Fabiger, Co., 1980.

EXAMPLE IX

Preparation of Polyurethane Tubing Having Both Bulk Distributed Chlorhexidine and a Surface Layer of Covalently Bound Heparin Polyurethane polymer pellets and 5% chlorhexidine diacetate were blended with the twin screw compounder and extruded into tubing as described in Example VIII. The tubing was then treated to provide a covalently bonded layer of heparin to both the inner and outer lumen surfaces using the method of Solomon et al., supra. This tubing demonstrated both antimicrobial and antithrombogenic properties similar to the tubing of Example VIII.

EXAMPLE X

Preparation of Polyurethane Tubing Having Both Bulk Distributed Chlorhexidine and Surface Bound Antibiotic Polyurethane polymer pellets and 5% chlorhexidine dihydrochloride were blended with the twin screw compounder and extruded into tubing as described in Example VIII. The tubing was then coated with ionically bonded dicloxicillin by the method of Solomon and Sherertz (supra) to both the inner and outer tubing surfaces. The resulting tubing had a bulk distributed broad spectrum antimicrobial (chlorhexidine) and a narrow layer of antibiotic with specific activity on the tubing surface. Other antibiotics specifically targeted for specific organisms may be used.

EXAMPLE XI

Preparation of Laminated Polyurethane Tubing with Bulk Distributed Chlorhexidine and Surface Bound Antibiotic Polyurethane tubing was prepared as described in Example VII with bulk distributed chlorhexidine in the outer tubing layer. Following tubing extrusion, the tubing was treated as described in Example X to provide an ionically bonded dicloxicillin coating to both the inner and outer tubing surfaces. This produced a tubing which had specific and broad antimicrobial action but without the presence of chlorhexidine in direct contact with the infusion fluid path.

EXAMPLE XII

Preparation of a Laminated Polyurethane Tubing with No Exterior Surface Distributed Chlorhexidine and with Surface Bound Antibiotic Polyurethane polymer pellets were bulk distributed with 5% chlorhexidine dihydrochloride by twin screw compounding. The melt was coextruded with resin containing no antimicrobial as described in Example VII, resulting in an inner layer with chlorhexidine, and an outer tubing layer with no chlorhexidine. Following extrusion, the tubing was treated as described in Example X to provide an ionically bonded clindamycin coating to both the inner and outer tubing surfaces.

EXAMPLE XIII

Preparation of Laminated Polyurethane Tubing Having Bulk Distributed Chlorhexidine and Silver Sulfadiazine A. Polyurethane polymer pellets and 5% chlorhexidine dihydrochloride were compounded via twin screw processing. Additional polyurethane pellets were compounded with 2% silver sulfadiazine. The two compounded resins were then coextruded into tubing such that the inner layer contained bulk distributed chlorhexidine, and the outer layer contained bulk distributed silver sulfadiazine. This tubing had one type of antimicrobial present on the outer surface, and a different antimicrobial present on the inner surface.

B. Polyurethane resins were prepared as in A and coextruded into tubing such that the inner layer contained bulk distributed silver sulfadiazine and the outer layer contained bulk distributed chlorhexidine.

EXAMPLE XIV

Preparation of Laminated Polyurethane Having Bulk Distributed Chlorhexidine Dihydrochloride But No Surface Layer of Chlorhexidine A melt of polyurethane pellets and 5% chlorhexidine dihydrochloride was prepared by twin screw compounding and triextruded with resin without antimicrobial to give antimicrobial tubing sandwiched between two non-antimicrobial layers.

EXAMPLE XV

Comparison of the flexibility of Polyolefins and Urethane Polymers

In accordance with the procedure of Zdrahala et al. (Polyurethanes in Biomedical Engineering, II, H. Planck et al., ed., Elsevier Science Publishers B. V. Amsterdam, 1987, p 1–18), pieces of 16 guage polyurethane (65D) and polypropylene tubing were tested for the effect of absorbed water on tubing stiffness on the Instron Model 1122 Universal Testing Machine. Bending forces in grams were determined after 24 hours under ambient conditions of 23° C. and 50% relative humidity and after soaking in normal saline for 24 hours at 23° C. The following results were obtained:

|  | Bending Force, gr | |
| --- | --- | --- |
|  | ambient | soak |
| polypropylene | 331 | 368 |
| polyurethane | 224 | 84 |

It is seen that a 24 hour soak had substantially no effect on the stiffness of the polypropylene tubing, but reduced the stiffness of the polyurethane by 62%.

Thus, the invention provides an anti-infective medical article fabricated from a high melting hydrophilic polymer having up to 10% of a chlorhexidine salt bulk distributed throughout the polymer. A preferred method to prepare the article includes blending of the polymer and the salt by twin screw compounding and extruding at high temperature.

What is claimed is:

1. A tubular medical article adapted for placement in contact with or insertion into living tissue comprising a polymeric inner lumen having a water absorption of at least 0.6% by weight and an anti-infective agent comprising a biguanide bulk distributed throughout.

2. The article of claim 1 further including silver sulfadiazine.

3. The article of claim 2, wherein said silver sulfadiazine is on an exterior surface of said article.

4. The article of claim 2, wherein said silver sulfadiazine is on the interior surface of said article.

5. The article of claim 2, wherein said silver sulfadiazine is bulk distributed throughout said polymeric inner lumen.

6. The article of claim 1, wherein said article further includes an antibiotic.

7. The article of claim 6, wherein said antibiotic is on a surface of said article.

8. The article of claim 7, wherein said antibiotic is on an interior surface of said article.

9. The article of claim 8, wherein said antibiotic is on an exterior surface of said article.

10. The article of claim 9, wherein said antibiotic is bulk distributed throughout said polymeric inner lumen.

11. The article of claim 10, further comprising an antithrombogenic agent.

12. The article of claim 12, wherein said antithrombogenic agent is on a surface of said article.

13. The article of claim 12, wherein said antithrombogenic agent is on an interior surface of said article.

14. The article of claim 13, wherein said antithrombogenic agent is on an exterior of said article.

15. The article of claim 14, wherein said antithrombogenic agent is bulk distributed throughout said polymeric inner lumen.

16. The article of claim 1, wherein said biguanide is selected from the group consisting of a chlorhexidine base and a chlorhexidine salt or mixtures thereof.

17. The article of claim 16, wherein said biguanide is a salt of chlorhexidine and said salt is selected from the group consisting of the hydrochloride, acetate and gluconate salts of chlorhexidine or mixtures thereof.

18. The article of claim 1, wherein said polymeric inner lumen is comprised of a polymer selected from the group consisting of polyurethane, siloxane-urethane block copolymer and polyurethaneurea.

19. The article of claim 16, wherein the concentration of said biguanide in said polymer is about 0.1 to 10% by weight.

20. The article of claim 1, further comprising a polymeric coating.

21. The article of claim 19, further comprising a polymeric coating.

22. The article of claim 1, which is a catheter.

23. A tubular medical article for contacting with or inserting into living tissue, comprising a polyurethane inner lumen having a water absorption of at least 0.6% by weight and a coating layer, the coating layer comprising a laminating polymer having a water absorption of at least 0.6% by weight, said inner lumen and laminating polymeric layers each having about 0.1 to 10% by weight of a biguanide bulk distributed throughout.

24. The article of claim 23, wherein said coating further comprises a second polymer having a water absorption of at least 0.6% by weight.

25. The article of claim 23, further including silver sulfadiazine.

26. The article of claim 25, wherein silver sulfadiazine is on the exterior surface of said article.

27. The article of claim 25, wherein said silver sulfadiazine is on the interior surface of said article.

28. The article of claim 25, wherein said silver sulfadiazine is bulk distributed throughout said laminating polymer.

29. The method article of claim 23, wherein said article further includes an antibiotic.

30. The article of claim 29, wherein said antibiotic is on a surface of said article.

31. The article of claim 29, wherein said antibiotic is on an interior surface of said article.

32. The article of claim 29, wherein said antibiotic is on an exterior surface of said article.

33. The article of claim 29, wherein said antibiotic is bulk distributed throughout said laminating polymer.

34. The article of claim 23, further comprising an antithrombogenic agent.

35. The article of claim 34, wherein said antithrombogenic agent is on a surface of said article.

36. The article of claim 34, wherein said antithrombogenic agent is on an interior surface of said article.

37. The article of claim 34, wherein said antithrombogenic agent is on an exterior surface of said article.

38. The article of claim 34, wherein said antithrombogenic agent is bulk distributed throughout said laminating polymer.

39. The article of claim 23, wherein said biguanide is selected from the group consisting of a chlorhexidine base and a chlorhexidine salt or mixtures thereof.

40. The article of claim 39, wherein said biguanide salt of chlorhexidine and said chlorhexidine is selected from the group consisting of the hydrochloride, acetate and gluconate salts of chlorhexidine or mixtures thereof.

41. The article of claim 23, wherein said polyurethane inner lumen comprises a polymer selected from the group consisting of polyurethane, siloxane-urethane block copolymer and polyurethaneurea.

42. The article of claim 23, wherein said laminating polymer is selected from the group consisting of polyurethane, siloxane-urethane block copolymer and polyurethaneurea.

43. The article of claim 23 which is a catheter.

* * * * *